| United States Patent [19] | [11] Patent Number: 4,783,469 |
|---|---|
| Meier et al. | [45] Date of Patent: Nov. 8, 1988 |

[54] METHOD OF INHIBITING BODY FAT STORES

[76] Inventors: Albert H. Meier, 6165 Chandler Dr., Baton Rouge, La. 70808; Anthony H. Cincotta, 3250 Carlotta St., No. 1, Baton Rouge, La. 70802

[21] Appl. No.: 84,903

[22] Filed: Aug. 13, 1987

Related U.S. Application Data

[63] Continuation-in-part of Ser. No. 40,188, Apr. 17, 1987, which is a continuation-in-part of Ser. No. 837,148, Apr. 17, 1986, Pat. No. 4,659,715.

[51] Int. Cl.[4] ............................................. A61K 31/44
[52] U.S. Cl. ................................................... 514/288
[58] Field of Search ........................................ 514/288

*Primary Examiner*—Stanley J. Friedman
*Attorney, Agent, or Firm*—E. E. Spielman; J. M. Pelton

[57] ABSTRACT

Methods for reducing body fat stores in vertebrate animals by administering a prolactin-inhibitor to the animal in a chosen dose which effects such reduction with or without a concomitant decrease in body weight is disclosed.

2 Claims, No Drawings

METHOD OF INHIBITING BODY FAT STORES

CROSS-REFERENCE TO A RELATED APPLICATION

This application is a continuation-in-part of our copending application, Ser. No. 040,188, filed Apr. 17, 1987, which in turn is a continuation-in-part of Ser. No. 837,148, filed Apr.17, 1986 and which has now issued as U.S. Pat. No. 4,659,715.

BACKGROUND OF THE INVENTION

This invention relates to methods for reducing body fat stores in vertebrate animals by administering to the animal an agent to suppress its prolactin secretion. The reduction in body fat stores can be accompanied with or without significant weight loss dependent upon the dosage received by the animal.

A method for reducing body fat stores accompanied by significant weight loss is valuable as a treatment for obesity in animals and humans which have attained undesirable and/or unhealthy body weights. Further, a method for reducing body fat stores without causing significant weight loss would be valuable to the livestock industry as a better grade of meat could be obtained without a concomitant lowering of the price paid per animal due to weight loss. In humans, such a method would be valuable to athletes who strive to obtain a low percentage of body fat without a loss in muscle mass.

It is, therefore, an object of this invention to provide such methods.

THE INVENTION

In accordance with a first embodiment of this invention, the body fat stores of a vertebrate animal can be reduced along with a loss in its body weight by administering to the animal an effective and a pharmaceutically appropriate dosage of an ergot-related prolactin inhibiting compound.

In accordance with a second embodiment of this invention, the body fat stores of a vertebrate animal can be reduced wthout substantial concomittant loss in its body weight by administering to the animal an effective and a pharmaceutically appropriate dosage, which dosage is greater than that given in the first embodiment for the same animal species, of an ergot-related prolactin inhibiting compound.

As can be seen from the above description of the two embodiments, the result obtained is dependent upon dosage. A theory, which is delineated in the following paragraph, to explain this dosage dependency is offered, it being understood, however, that the methods of this invention are not to be limited thereby.

At one dosage level, as in the first embodiment, ergot-related prolactin inhibiting compounds, e.g., 2-bromo-α-ergocryptine, are potent dopamine agonists and, as such, can directly inhibit prolactin release without substantially altering growth hormone release. At higher dosages, as in the second embodiment, these compounds can stimulate growth hormone and cortisol release while still inhibiting prolactin release. In both embodiments, inhibition of prolactin release can be expected to result in a decrease in body fat stores and thus body weight as prolactin maintains hepatic lipogenic responsiveness to insulin at least in part by maintaining high numbers of insulin receptors. Reduction of prolactin secretion by the methods of both embodiments result in decreased hepatic lipogenesis and loss of lipogenic responsiveness to insulin. Also, the hepatic insulin receptor number is also severely reduced. At the high dosages, as in the second embodiment, in which there is inhibition of prolactin release and stimulation of growth hormone and cortisol release, the reduction of body fat weight, caused by inhibition of prolactin release, may be replaced by muscle weight as a result of increased growth hormone and cortisol release. Therefore, at the higher dosages, body fat stores would be reduced without altering body weight. Of course in the first embodiment, since there is no enhancement of growth hormone and cortisol release, there is no replacement by muscle weight of the body fat stores lost due to the administration of the ergot-related compound.

The dosing of the animal with the ergot-related compounds may be by oral or by parenteral, e.g., subcutaneous or intramuscular injection, administration.

Exemplary of ergot-related prolactin-inhibitors are: 2-bromo-α-ergocryptine; 6-methyl-8β-carbobenzyloxyaminomethyl-10 -ergoline; 1,6-dimethyl-8β-carbobenzyloxy-aminomethyl-10α-ergoline; 8-acylaminoergolenes, such as 6-methyl-8α-(N-acyl)amino-9-ergolene and 6-methyl-8α-(N-phenylacetyl)amino-9-ergolene; ergocornine; 9,10-dihydroergocornine; and D-2-halo-6-alkyl-8-substituted ergolines, e.g., D-2-bromo-6-methyl-8-cyanomethylergoline. The foregoing ergot-related compounds and the processes for their formation are known to the art. From the standpoint of side effects, especially that on fertility, 2-bromo-α-ergocryptine has been found to be highly suitable for the methods of this invention.

The non-toxic salts of the prolactin-inhibiting ergot-related compounds formed from pharmaceutically acceptable acids are also useful in the method of this invention.

When dosed with ergot-related compounds of this invention different animal species exhibit dissimilar sensitivities to prolactin-inhibition and growth hormone-inhibition, as is theorized to occur for the first embodiment, and to prolactin-inhibition and growth hormone/cortisol-stimulation, as is theorized to occur for the second embodiment. Hence, when considering all species of vertebrate animals as a single group, the dosage required to obtain reductions in body fat stores with weight loss and the dosage required to obtain reductions in body fat without significant weight loss both vary over a fairly wide range. Exemplifying such is the finding that, for the first embodiment, in Djungarian Hamsters, a dosage of 125 ug/day of 2-bromo-α-ergotcryptine was effective but that, in Black Mice, a dosage of 360 ug/day of 2-bromo-α-ergotcryptine was needed to be effective. Further, it has been found for each embodiment of this invention that the proper dosage range for a selected animal species also can be quite wide. For example, in the case of the second embodiment, a study of golden hamsters showed that an intraperitoneal daily dose, as low as 0.15 mg/kg body weight and as high as 6.00 mg/kg of body weight, of 2-bromo-α-ergocryptine in divided doses of two times a day for a 24-day period gave good reductions in body fat stores without significant losses in body weight. Thus, considering the foregoing, it can be seen that the suitable dosage range is best determined empirically for each animal species and for each embodiment. Generally, the minimum dosage needed in each embodiment to obtain the effect sought will be the preferred dosage as the chance of unwanted side effects is diminished and the cost of dosing will be kept to a minimum.

Capsules or tablets containing the unit doses of the ergot-related compounds are suitable for oral dosing. Generally, the ergot-related compounds will be used as a pharmaceutically acceptable salt when administered orally. If parenteral dosing or implantation is used, the ergot-related compound will be provided with conventional sterile diluents, such as, mannitol, sucrose, vegetable oil, etc. The duration of administration may vary from species to species but is as long as is needed for the first embodiment, to obtain the final body weight sought and is generally at least 7 days in length for the second embodiment.

In both embodiments, if the animals being treated are for commercial slaughtering, e.g., the animals are swine or ruminants, the period of time for dosage should be at least 7 days, and preferably at least 10 days, in length and up to the fifth day before slaughter. The minimum 7 day dosing period is believed generally necessary to effect a commercially significant change in the commercial animal being treated. It is believed desirable to cease dosing five days before slaughter to allow the ergot-related prolactin-inhibitor to be substantially eliminated from the animal's system at the time of slaughter. If the animal is being subjected to long-term treatment, in accordance with the second embodiment of this invention, then the dosing is first given at an initial level for that period of time necessary to achieve the desired body fat stores and is thereafter dosed, usually at a lower level, so as to maintain the achieved body fat stores for the extended period.

EXAMPLE I

This Example illustrates the method of the second embodiment of this invention. Mature (3–7 months old) male golden hamsters, *Mesocricetus auratus* (body weight: 100–150 g) were caged in pairs, fed ad libitum, maintained at 23° C. and provided 14-h daily photoperiods (light onset: 0800h). The hamsters were injected (i.p.) daily at 0800 and 1400 with 2-bromo-α-ergocryptine (300 ug/0.1 ml peanut oil) or peanut oil (controls). Food consumption was monitored daily. After 24 days of treatment, the animals were killed by overdose of sodium pentobarbital to obtain body weights, abdominal and epididymal fat pad weights, and testes and seminal vescicle weights. Statistical differences between the two groups were tested by Student's t to determine the significance, "P". The results are given in the table.

In the Examples shown in Table I, the 2-bromo-α-ergocryptine treatment reduced ($P<0.01$) abdominal fat weight 47% and epididymal fat weight 32% compared with control treatment. However, 2-bromo-α-ergocryptine did not alter body weight, food consumption, paired testes weights or seminal vescicle weights. The constancy of testes and seminal vescicle weights is good indication that the 2-bromo-α-ergocryptine treatment of this invention has no effect on the animals' fertility.

Since body weight was not adversely affected by treatment with 2-bromo-α-ergocryptine, it is apparent that the method of this invention causes the animal to direct metabolic energy away from lipogenesis and towards protein formation.

For the Examples shown in Table II, the treatment was for 10 days using the same dosage and prolactin-inhibitor as was used for the Examples of Table I. The animals had an initial average body weight of 100 g.

TABLE I

| | | BODY WT. | INDICES OF BODY FAT STORES | | | | LIVER WT. |
| --- | --- | --- | --- | --- | --- | --- | --- |
| | | | EPIDIDYMAL FAT PAD | | ABDOMINAL FAT PAD | | |
| TREATMENT | N | (% INCR.) | (g) | (% B.W.) | (g) | (% B.W.) | (g) |
| Experiment 1 - (3–4 month of age) | | | | | | | |
| Control | 9 | 11.5 ± 4.0 | 1.73 ± 0.06 | 1.37 ± 0.05 | 0.84 ± 0.03 | 0.67 ± 0.03 | 5.2 ± 0.2 |
| 2-Bromo-α-ergocryptine (6.00 mg/kg/day) | 10 | 16.3 ± 2.4 | 1.17 ± 0.07[1] | 0.93 ± 0.05[1] | 0.43 ± 0.02[1] | 0.38 ± 0.01[1] | 5.3 ± 0.3 |
| Experiment 2 - (7 months of age) | | | | | | | |
| Control | 8 | 3.3 ± 0.9 | 1.35 ± 0.07 | 1.10 ± 0.05 | 0.96 ± 0.08 | 0.77 ± 0.06 | 4.9 ± 0.5 |
| 2-Bromo-α-ergocryptine (6.00 mg/kg/day) | 8 | 5.4 ± 1.2 | 1.07 ± 0.09[2] | 0.76 ± 0.04[1] | 0.72 ± 0.07[2] | 0.54 ± 0.04[1] | 5.6 ± 0.7 |
| 2-Bromo-α-ergocryptine (2.00 mg/kg/day) | 7 | 3.0 ± 1.1 | 1.08 ± 0.05[1] | 0.90 ± 0.05[1] | 0.75 ± 0.08[3] | 0.63 ± 0.08[3] | 5.0 ± 0.3 |
| 2-Bromo-α-ergocryptine (0.15 mg/kg/day) | 8 | 1.6 ± 1.2 | 0.91 ± 0.06[1] | 0.86 ± 0.05[1] | 0.60 ± 0.04[1] | 0.56 ± 0.04[1] | 4.5 ± 0.2 |

| | | FOOD CONSUMED | REPRODUCTIVE INDICES | | |
| --- | --- | --- | --- | --- | --- |
| TREATMENT | N | (g/day/animal) | TESTES (g) | SEMINAL VESICLES (g) | ACCESSORY SEX ORGAN (g) |
| Experiment 1 - (3–4 months of age) | | | | | |
| Control | 9 | 8.8 ± 0.2 | 4.0 ± 0.1 | 1.62 ± 0.08 | 0.98 ± 0.10 |
| 2-Bromo-α-ergocryptine (6.00 mg/kg/day) | 10 | 8.8 ± 0.2 | 3.9 ± 0.1 | 1.68 ± 0.10 | 0.90 ± 0.10 |
| Experiment 2 - (7 months of age) | | | | | |
| Control | 8 | 10.4 ± 0.3 | 3.5 ± 0.2 | 1.42 ± 0.05 | 0.84 ± 0.05 |
| 2-Bromo-α-ergocryptine (6.00 mg/dg/day) | 8 | 11.2 ± 0.3 | 3.6 ± 0.2 | 1.53 ± 0.06 | 0.78 ± 0.06 |
| 2-Bromo-α-ergocryptine (2.00 mg/kg/day) | 7 | 9.8 ± 0.3 | 3.3 ± 0.2 | 1.57 ± 0.03 | 0.79 ± 0.05 |
| 2-Bromo-α-ergocryptine | 8 | 9.2 ± 0.5 | 3.3 ± 0.1 | 1.40 ± 0.07 | 0.76 ± 0.06 |

TABLE I-continued (0.15 mg/kg/day)

[1] Significantly less than control (P less than 0.01)
[2] Significantly less than control (p less than 0.05)
[3] Not significantly different from control
[4] Number of hamsters.

TABLE II

INDICES OF BODY FAT STORES

| TREATMENT | N | FINAL BODY WT. | EPIDIDYMAL FAT PAD (g) | EPIDIDYMAL FAT PAD (% B.W.) | ABDOMINAL FAT PAD (g) | ABDOMINAL FAT PAD (% B.W.) | LIVER WT. (g) | FOOD CONSUMED (g/day/animal) |
|---|---|---|---|---|---|---|---|---|
| Experiment 1 - (3-4 months of age) | | | | | | | | |
| Control | 5 | 116 ± 12 | 1.23 ± 0.08 | | 0.88 ± 0.08 | | 4.5 ± 0.2 | |
| 2-Bromo-α-ergocryptine (6.00 mg/kg/day) | 5 | 109 ± 7 | 0.85 ± 0.14[1] | | 0.42 ± 0.06[1] | | 4.3 ± 0.3 | |
| Experiment 2 - (3-4 months of age) | | | | | | | | |
| Control | 5 | 103 ± 6 | 1.50 ± 0.18 | 1.43 ± 0.11 | 1.17 ± 0.22 | 1.10 ± 0.16 | | 8.6 |
| 2-Bromo-α-ergocryptine (6.00 mg/kg/day) | 5 | 91 ± 3 | 0.98 ± 0.05[1] | 1.07 ± 0.04[1] | 0.46 ± 0.05[1] | 0.50 ± 0.05[1] | | 8.5 |

[1] Significantly less than control (P < 0.05).
N Number of Hamsters

EXAMPLE II

This Example illustrates the method of the first embodiment of this invention. The procedure of Example I was followed except that the vertebrate animals were female Djungarian Hamsters approximately 6 months of age and having a body weight within the range of 20 to 25 grams. Also, in this Example II, the treatment was for 15 days with twice-a-day injections of 62.5 ug 2-bromo-α-ergocryptine in 0.05 ml of peanut oil. The results which are shown in Table III show that there were significant (P<0.05, students T) losses in body weight and in the indices of body fat. This shows that the treatment reduced both body weight and body fat stores.

TABLE III

| | Body Weight | | | Indices of Body Fat | | Food Consumption |
|---|---|---|---|---|---|---|
| Treatment | Initial (g) | Final (g) | % Change | Uterine Fat (mg) | Abdominal Fat (mg) | (g/animal/day) |
| Control | 24.0 ± 0.4 | 26.4 ± 1.0 | +9.2 ± 4.7 | 200 ± 41 (0.75% B.W.) | 117 ± 25 (0.44% B.W.) | 3.2 ± 0.2 |
| Bromocriptine (125 ug/day) | 23.0 ± 1.2 | 21.0 ± 1.2* | −7.1 ± 3.8* | 82 ± 8* (0.39% B.W.) | 46 ± 9* (0.17% B.W.) | 3.0 ± 0.1 |

*Values differ significantly from control values (P < 0.5, student's t).

EXAMPLE III

This Example illustrates the method of the first embodiment of this invention. The procedure of Example I was followed except that the vertebrate animals were female Black Mice, *Mus Musculus*, which were 8 to 12 months of age and had a body weight between 20 and 30 grams. Also, the treatment period was for 14 days and the dosage was twice a day of 180 ug of 2-bromo-α-ergocrytine and 0.05 ml of peanut oil. Further, the photoperiods were twelve hours with light onset at 0600 to 1800 hours. As can be seen in Table IV, there was significant (P,<0.05, students T) loss in body weight. Also, a loss in body fat was seen.

TABLE IV

| | Body Weight | | | Indices of Body Fat Uterine Fat + Abdominal Fat (mg) | Food Consumption (g/animal/day) |
|---|---|---|---|---|---|
| Treatment | Initial (g) | Final (g) | % Change | | |
| Control | 27.3 ± 0.4 | 28.8 ± 0.4 | +5.9 ± 1.9 | 650 ± 42 | 2.8 ± 0.02 |
| Bromocriptine (360 ug/day) | 25.7 ± 0.9 | 23.9 ± 1.0* | −7.4 ± 1.2* | 525 ± 59 | 3.2 ± 0.07 |

*Values differ significantly from control values (P <-.05, students's t).

We claim:

1. A method for treating a vertebrate animal to reduce its body fat stores with concomintant loss in its body weight, which method comprises administering to a vertebrate animal in need of such treatment an effective dosage of an ergot-related prolactin-inhibiting compound, which dosage level is less than that required to stimulate growth hormone, said administration being carried out for a period sufficient for animal to obtain a predetermined body weight which is less than its pretreatment body weight.

2. The method of claim 1 wherein said ergot-related prolactin inhibiting compound is 2-bromo-α-ergocryptine or its salts formed from pharmaceutically acceptable acids.

* * * * *

UNITED STATES PATENT AND TRADEMARK OFFICE
CERTIFICATE OF CORRECTION

PATENT NO. : 4,783,469
DATED : November 8, 1988
INVENTOR(S) : Albert H. MEIER et al.

It is certified that error appears in the above-indentified patent and that said Letters Patent is hereby corrected as shown below:

On the title page, item: 63], Related U.S. Application Data, change ."Apr. 17" to --Mar. 7--.
    Col. 9, line 7, change "Apr. 17" to --Mar. 7--.

Signed and Sealed this

Seventh Day of October, 1997

Attest:

BRUCE LEHMAN

Attesting Officer      Commissioner of Patents and Trademarks